(12) United States Patent
Walsdorff et al.

(10) Patent No.: US 7,186,395 B2
(45) Date of Patent: Mar. 6, 2007

(54) IRON OXIDES WITH A HIGHER DEGREE OF REFINING

(75) Inventors: Christian Walsdorff, Ludwigshafen (DE); Michael Bajer, Mannheim (DE); Reinhard Körner, Frankenthal (DE); Klaus Harth, Altleiningen (DE); Gerald Vorberg, Speyer (DE); Wilhelm Ruppel, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 421 days.

(21) Appl. No.: 10/473,214

(22) PCT Filed: Apr. 3, 2002

(86) PCT No.: PCT/EP02/03672

§ 371 (c)(1),
(2), (4) Date: Sep. 29, 2003

(87) PCT Pub. No.: WO02/083569

PCT Pub. Date: Oct. 24, 2002

(65) Prior Publication Data

US 2004/0097768 A1   May 20, 2004

(30) Foreign Application Priority Data

Apr. 10, 2001 (DE) ................. 101 17 996
Nov. 9, 2001 (DE) ................. 101 54 718

(51) Int. Cl.
*B10J 23/745* (2006.01)
*C07C 5/32* (2006.01)
*C01G 49/00* (2006.01)

(52) U.S. Cl. ............... 423/632; 423/138; 423/150.3; 423/633; 423/DIG. 1; 502/325; 585/440; 585/444

(58) Field of Classification Search ............... 423/138, 423/150.3, 632, 633, DIG. 1; 502/325, 304, 502/330, 328, 305; 585/440, 444, 445
See application file for complete search history.

(56) References Cited

U.S. PATENT DOCUMENTS

| 2,414,585 A | | 1/1947 | Eggertsen et al. |
| 4,134,858 A | | 1/1979 | Courty |
| 5,597,547 A | * | 1/1997 | Hamilton, Jr. ............... 423/632 |
| 5,911,967 A | * | 6/1999 | Ruthner ....................... 423/632 |
| 6,210,650 B1 | * | 4/2001 | Karner et al. ................ 423/488 |
| 6,551,958 B1 | * | 4/2003 | Baier et al. .................. 502/304 |

FOREIGN PATENT DOCUMENTS

| CA | 2026120 | | 3/1991 |
| CA | 2298227 A1 | * | 8/2000 |
| EP | 297 657 | | 1/1989 |
| EP | 419 964 | | 4/1991 |
| EP | 797 481 | | 10/1997 |
| EP | 827 488 | | 3/1998 |
| EP | 1 027 928 | | 8/2000 |
| EP | 1027928 A1 | * | 8/2000 |
| JP | 61-72601 A | * | 4/1986 |
| WO | 95/25069 | | 9/1995 |

OTHER PUBLICATIONS

DialogWeb Guided Search of CA 2,298,227 A dated Aug. 10, 2000, 4 pages.*
Derwent abstract for EP 850,881 A1 dated Jul. 1, 1998, 3 pages.*
Derwent JP 61072-601 Abstract.
XP-002216178.
XP-002216007.
61146719 Patent Abstract of Japan.

* cited by examiner

*Primary Examiner*—Timothy C. Vanoy
(74) *Attorney, Agent, or Firm*—Novak Druce & Quigg LLP

(57) ABSTRACT

Iron oxides are upgraded by calcining at from 700 to 1200° C.

8 Claims, No Drawings

IRON OXIDES WITH A HIGHER DEGREE OF REFINING

DESCRIPTION

The present invention relates to a process for upgrading iron oxide, which comprises calcining iron oxide at not less than 700° C.

EP-A-1 027 928 describes a catalyst, especially for dehydrogenation of ethylbenzene to styrene, which is prepared using an iron oxide obtained by spray roasting an iron salt solution, especially hydrochloric acid iron solutions (Ruthner process). The disadvantage of such iron oxides is their high residual chloride content.

EP-A-797 481 discloses iron oxides as a starting material for catalysts, especially for dehydrogenation of ethylbenzene to styrene, which are restructured by mixing with a further metal compound and subsequent calcination and which have very small BET surface areas. The disadvantage of such a restructuring is the contamination of the iron oxide by the metal compound added.

JP-A-61-72601 discloses a fluidized bed process for cracking heavy hydrocarbons into lighter hydrocarbons using a pulverulent catalyst prepared by slurrying up an iron oxide powder with water, spray drying and finally calcining at temperatures between 1200 and 1600° C. Disadvantages of this process are the immense cost and inconvenience and the high calcination temperatures.

EP-A-827 488 describes a process for reducing the residual chloride content in iron oxides, especially in iron oxides generated by spray roasting hydrochloric acid pickling wastes, by mixing the iron oxide with a hydrated metal compound and subsequent calcination. The disadvantage of this process is its cost and inconvenience.

U.S. Pat. No. 4,134,858 discloses roasting iron oxide at 800° C. before using it to prepare styrene catalysts. However, any residual chloride content in the iron oxide cannot be sufficiently lowered by this method.

U.S. Pat. No. 2,414,585 discloses precalcining iron oxide for preparing dehydrogenation catalysts. The iron oxide obtained is said to have a BET surface area of <8 m²/g and preferably of about 4 m²/g. Such catalysts leave a lot to be desired.

It is an object of the present invention to remedy the aforementioned disadvantages.

We have found that this object is achieved by a novel and improved process for upgrading iron oxide, which comprises calcining iron oxides at from 700 to 2500° C. The invention further provides novel iron oxides and their use as catalysts, and for the preparation of catalysts, especially for the preparation of catalysts for dehydrogenation of ethylbenzene to styrene.

The process of the invention can be carried out as follows:

The upgrading of the present invention may be applied to any iron oxide, but is preferably applied to iron oxides generated by working up hydrochloric acid waste liquids from steel pickling, for example, especially iron oxides generated by spray roasting hydrochloric acid pickling wastes (Ruthner process).

The iron oxide may be subjected to a batch operated or preferably continuous calcination at from 700 to 1200° C., preferably at from 840 to 1150° C., particularly preferably at from 850 to 1100° C., especially at from 860 to 1000° C., or generally from 0.1 to 24 h, preferably from 0.25 to 10 h, particularly preferably from 0.3 to 5 h, especially from 0.5 to 1.5 hr, without pretreatment, i.e., for example without mechanical pretreatment, and preferably dry, i.e., without prior treatment with water, an acid or base or some other material. Useful calcination apparatus includes all known ovens. The calcination can be carried out batchwise, for example in muffle furnaces, or continuously, for example in rotary tube ovens or in belt calciners. Preference is given to continuous processes. The calcination can be carried out at just one temperature or in stages at various temperatures or in the form of a continuous temperature ramp. When the calcination is carried out in rotary tubes, the rotary tube should be equipped with tappers which prevent sticking of the iron oxide to the wall of the rotary tube and ensure continuous transportation of the iron oxide. Advantageously, the calcination is carried out in smooth rotary tubes without internal fitments, and the residence time can be adjusted via the speed of rotation, the feed speed and the inclination of the rotary tube. The calcination is further advantageously carried out under a gas stream, for example nitrogen or air, in order that chlorine compounds being released may be expelled and advantageously removed in a downstream off-gas scrub. The chloride content is advantageously reducible in a stationary bed, i.e., for example in the course of calcination in a muffle furnace or on a belt calciner. When a calcination is carried out in a moving bed, for example in a rotary tube, comparatively somewhat higher temperatures can be required to reduce the chloride content than in a stationary bed, and this can lead to a comparatively further reduced BET surface area. Depending on the preferred ratio of chloride content and BET surface area, it can therefore be advantageous to operate selectively with a stationary bed or with a moving bed.

However, small amounts of water, acids, bases or organic compounds may be added, provided this does not adversely affect the properties of the upgraded iron oxide compared to a dry upgrading process. Preference is given to calcining commercially available iron oxide without any pretreatment whatever.

Useful iron oxides for the upgrading according to the invention include all iron oxides, regardless of how obtained. Natural, preferably industrially produced and also commercially available iron oxides are suitable, especially iron oxides generated by working up hydrochloric acid pickling wastes. These iron oxides maybe contain impurities, for example a residual chloride content and/or compounds of titanium, manganese, aluminum, chromium, phosphorus, zinc, copper, molybdenum, tungsten, silicon, nickel, magnesium, potassium, sodium, cobalt, vanadium, zirconium, niobium, sulfur, lanthanum, lead, tin and/or calcium. Of particular suitability are iron oxides which are generated by spray roasting hydrochloric acid pickling wastes in the steel industry and are present as $Fe_2O_3$ having a residual chloride content in the range from 0 to 10 000 ppm, preferably in the range from 50 to 5000 ppm and particularly preferably in the range from 500 to 2000 ppm, usually in the hematite crystal form and in a BET surface area of typically from 3 to 5 m²/g.

Iron oxides upgraded according to the invention generally have a residual chloride content of less than 400 ppm, preferably less than 300 ppm and particularly preferably less than 250 ppm, especially less than 200 ppm. The average particle size, determined by laser diffraction as hereinbelow described, is generally more than 5 µm, i.e., from 5.1 to 200 µm, preferably from 8 to 100 µm, particularly preferably from 10 to 80 µm and very particularly preferably from 12 to 30 µm, and the fines fraction having particle sizes of less than 1 µm is generally less than 15% by weight, preferably less than 10% by weight, particularly preferably less than 5% by weight. The BET surface area of the iron oxides treated according to the invention is generally in the range from 0.4 to 5 m²/g, preferably in the range from 0.4 to 3.5 m²/g, particularly preferably in the range from 0.5 to 3 m²/g and especially in the range from 0.6 to 2.5 m²/g, very particularly preferably in the range from 0.7 to 2 m²/g. The iron oxides treated according to the invention generally have a hematite structure. They are useful for a whole series of industrial applications such as pharmaceuticals, cosmetics, magnetic tape coatings, chemical reactions, catalysts or for preparing catalysts, especially for preparing catalysts for dehydrogenation of ethylbenzene to styrene.

The industrial production of styrene by dehydrogenation of ehtylbenzene can be effected by isothermal processes or by adiabatic processes. The isothermal process is generally operated at from 450 to 700° C., preferably from 520 to 650° C., in the gas phase with addition of water vapor at from 0.1 to 5 bar, preferably from 0.2 to 2 bar, particularly preferably from 0.3 to 1 bar, especially from 0.4 to 0.9 bar. The adiabatic process is generally operated at from 450 to 700° C., preferably from 520 to 650° C., in the gas phase with addition of water vapor at from 0.1 to 2 bar, preferably from 0.2 to 1 bar, particularly preferably from 0.3 to 0.9 bar, especially from 0.4 to 0.8 bar. Catalysts for the dehydrogenation of ethylbenzene to styrene can be regenerated by means of water vapor.

Catalysts for the dehydrogenation of ethylbenzene to styrene generally contain iron oxide and an alkali metal compound, for example potassium oxide. Such catalysts generally further contain a number of promoters. Promoters described include for example compounds of calcium, magnesium, cerium, molybdenum, tungsten, chromium and titanium. The catalysts may be prepared using compounds of the promoters that will be present in the ready-produced catalyst or compounds which during the production process convert into compounds that are present in the ready-produced catalyst. The materials used may also include assistants to improve the processibility, the mechanical strength or the pore structure. Examples of such assistants include potato starch, cellulose, stearic acid, graphite or Portland cement. The materials used can be mixed directly in a mixer, kneader or preferably a muller. They can also be slurried up into a sprayable mix and be spray dried to form a powder. The materials used are preferably processed in a muller or kneader in the presence of water to form an extrudable mass. The extrudable mass is subsequently extruded, dried and calcined. Preferred extrudates are from 2 to 10 mm in diameter. The cross section of the extrudates may be round or some other shape. Particular preference is given to extrudates having a rotationally symmetrical cross section, especially 3 mm in diameter, and also extrudates having a star-shaped cross section or a toothed-wheel cross section, especially 4.5 or 6 mm in diameter. The extrudates can be broken or cut. As an alternative to an extrusion, the catalysts may also be shaped by tableting. Generally, the catalysts prepared according to the invention have larger mean pore radii and a smaller BET surface area than catalysts otherwise prepared similarly, but from iron oxide not upgraded according to the invention.

Catalysts prepared using the iron oxide upgraded according to the invention instead of conventional, prior art iron oxide exhibit improved activity and selectivity. The fraction of iron oxide pretreated according to the invention as a percentage of all the iron oxide present in the catalyst should be not less than 30% by weight, preferably not less than 60% by weight and very particularly preferably not less than 90% by weight. It is especially preferred for the fraction of iron oxide upgraded according to the invention as a percentage of the total iron oxide content to be 100% by weight. Catalysts for the dehydrogenation of ethylbenzene to styrene which have been prepared using iron oxide upgraded according to the invention are useful in all processes and process variants. They are particularly useful at steam/ethylbenzene (S/EB) ratios of from 0.6 to 2.5 kg/kg. They are very particularly useful at steam/ethylbenzene ratios of from 0.9 to 1.5 kg/kg. The catalysts prepared according to the invention are notable for a low chloride content of less than 500 ppm, typically less than 300 ppm, particularly less than 200 ppm and an average pore diameter of from 0.3 to 3 μm, typically from 0.5 to 1.5 μm.

EXAMPLES

Inventive example 1 and comparative example A utilized the HP (Hōsch Premium) iron oxide from Thyssen-Krupp, which is produced according to the Ruthner process by spray roasting hydrochloric acid iron solutions. The residual chloride content was in all cases determined coulometrically. The particle size of the iron oxide was determined using a Mastersizer S from Malvern (lense: 300 RFmm, measuring range 0.05 to 880 μm). The MS17 model was used. It is a sample feeder for dispersion in an aqueous medium having a built-in paddle stirrer, an integrated ultrasonic probe and a circulation pump. Prior to the measurement, the integrated ultrasonic bath (100% setting) was started up and, following a dispersion time of 5 min, the measurement was carried out under continuing ultrasonication. Specific BET surface areas were determined according to DIN 66133 and pore volumes and average pore radii according to DIN 66131.

Inventive Example 1

2 kg of HP type iron oxide from Thyssen-Krupp were heated to 900° C. in a muffle furnace, left in the oven at this temperature for 1 h and subsequently allowed to cool down with the oven.

Inventive Example 2

Inventive example 1 was repeated at 800° C.

Inventive Example 3

Inventive example 1 was repeated at 850° C.

Inventive Example 4

Inventive example 1 was repeated at 950° C.

Inventive Example 5

20 g of HP type iron oxide from Thyssen-Krupp were heated to 900° C. in a quartz glass rotary tube under an air stream, maintained therein at 900° C. for 1 h and then allowed to cool down therein.

Inventive Example 6

Inventive example 5 was repeated, except that the iron oxide was maintained at 900° C. for 2 h.

Inventive Example 7

The iron oxide was continuously calcined under an air stream in a rotary tube. The rotary tube was equipped with three tappers. The wall temperature of the rotary tube was 970° C. and the residence time of the iron oxide was about one hour.

The physical properties of the inventively pretreated iron oxides of inventive examples 1 to 7 are summarized in table 1 and compared therein with those of the nonupgraded iron oxide.

Inventive Example 8

A spray slurry prepared by suspending 420 g of potassium carbonate (potash), 516 g of cerium carbonate hydrate (40% by weight cerium content), 74 g of ammonium heptamolybdate, 70 g of calcium hydroxide (white chalk hydrate), 55 g of magnesite and 1880 g of the iron oxide upgraded according to inventive example 1 in 4.5 liters of water was sprayed to form a powder which was pasted up with sufficient water (about 500 ml) in the presence of starch in a kneader to form an extrudable mass which was extruded into strands 3 mm in diameter. The strands were then dried at 120° C., broken to a length of about 0.8 mm and finally calcined in a rotary tube at 875° C. for 1 h.

Inventive Example 9

415 ml of a catalyst of inventive example 2 were tested in an externally heated tubular reactor 3 cm in internal diameter under the conditions reported in table 3.

Comparative Example A

A catalyst was prepared similarly to inventive example 8 except that the upgraded iron oxide of inventive example 1 was replaced by nonupgraded iron oxide (HP type from Thyssen-Krupp).

Comparative Example B 415 ml of the catalyst of comparative example A were tested similarly to inventive example 3 in the same reactor under the same conditions. The results are summarized in table 3.

TABLE 1

Properties of a commercially available iron oxide prepared by the Ruthner process (type HP from Thyssen-Krupp) and of iron oxides prepared therefrom by the upgrading according to the invention from inventive examples 1 to 7.

| Iron oxide | Residual chloride [ppm] | Average particle size [μm] | Fines less than 1 mm [% by weight] | BET surface area [m²/g] |
|---|---|---|---|---|
| Untreated HP type (Thyssen-Krupp) | 1400 | 11 | 15 | 4.3 |
| Inventive example 1 | 66 | 19 | 2 | 1.4 |
| Inventive example 2 | 240 | 15 | 2.5 | 2.1 |
| Inventive example 3 | 110 | 18 | 1.7 | 1.8 |
| Inventive example 4 | 19 | 22 | 1 | 1.1 |
| Inventive example 5 | 230 | — | — | 1.6 |
| Inventive example 6 | 190 | — | — | 0.7 |
| Inventive example 7 | 190 | 13 | 1.9 | 0.9 |

TABLE 2

Comparison of physical properties of the catalyst of inventive example 2, prepared using an iron oxide upgraded according to the invention, and of the catalyst of comparative example A, prepared according to the prior art.

| | BET surface area [m²/g] | Pore volume [ml/g] | Average pore diameter [μm] | Cut resistance [N] |
|---|---|---|---|---|
| Inventive example 8 | 1.3 | 0.27 | 1.28 | 64 |
| Comparative example A | 2.9 | 0.25 | 0.39 | 51 |

TABLE 3

Comparison of conversion and selectivity for dehydrogenation of ethylbenzene to styrene using an inventive catalyst (inventive example 3) and a prior art catalyst (comparative example B).

| LHSV [h⁻¹] | Pressure abs. [bar] | Steam/EB ratio [kg/kg] | Temperature [° C.] | Inventive example 9 EB conversion (styrene selectivity) | Comparative example B EB conversion (styrene selectivity) |
|---|---|---|---|---|---|
| 0.85 | 0.5 | 1.4 | 590 | 70.2% (96.2%) | 68.3% (96.1%) |
| 0.85 | 0.5 | 1.4 | 570 | 54.5% (97.2%) | 53.9% (97.2%) |
| 0.45 | 0.5 | 1.5 | 550 | 46.7% (97.4%) | 45.7% (97.2%) |
| 0.45 | 0.4 | 1.1 | 550 | 46.2% (97.9%) | 41.5% (97.9%) |

The invention claimed is:

1. A process for upgrading an iron oxide, comprising:
   working up hydrochloric acid pickling waste to generate iron oxide, and
   calcining the generated iron oxide at a temperature from 840 to 1150° C., optionally under nitrogen or air stream without the addition of other substances, wherein calcination is conducted without mechanical pretreatment, without prior treatment with water and without prior treatment with an acid or a base.

2. A process as claimed in claim 1, wherein said iron oxide is calcined at from 850 to 1000° C.

3. A process as claimed in claim 1, wherein the calcining is effected using a rotary tube equipped with tappers.

4. The process as claimed in claim 1, wherein the upgraded iron oxide has a residual chloride content of less than 400 ppm.

5. The process as claimed in claim 1, wherein the upgraded iron oxide has a chloride content of less than 200 ppm.

6. The process as claimed in claim 1, wherein the upgraded iron oxide has an average particle size of more than 5 μm.

7. A process for preparing a catalyst comprising:
   working up hydrochloric acid pickling waste to generate iron oxide,
   calcining the generated iron oxide at a temperature from 840 to 1150° C., optionally under nitrogen or air stream without the addition of other substances, wherein calcination is conducted without mechanical pretreatment, without prior treatment with water and without prior treatment with an acid or a base, and wherein the iron oxide has a residual chloride content of less than 400 ppm; and
   processing the calcined iron oxide to obtain the catalyst.

8. A dehydrogenation process comprising:
generating styrene by dehydrogenating ethylbenzene at a temperature of from 450 to 700° C. and a pressure of from 0.1 to 5 bars with a catalyst, wherein said catalyst is made by a process comprising:
working up hydrochloric acid pickling waste to generate iron oxide,
calcining the generated iron oxide at a temperature from 840 to 1150° C., optionally under nitrogen or air stream without the addition of other substances, wherein calcination is conducted without mechanical pretreatment, without prior treatment with water and without prior treatment with an acid or a base, and wherein the iron oxide has a residual chloride content of less than 400 ppm; and
processing the calcined iron oxide to obtain the catalyst.

* * * * *